United States Patent
Ta et al.

(10) Patent No.: US 10,238,513 B2
(45) Date of Patent: Mar. 26, 2019

(54) INTRAVASCULAR STENT

(71) Applicant: Abbott Cardiovascular Systems Inc., Santa Clara, CA (US)

(72) Inventors: Diem Uyen Ta, San Jose, CA (US); Erik D. Eli, Redwood City, CA (US); Nianjiong Joan Bei, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 56 days.

(21) Appl. No.: 15/653,972

(22) Filed: Jul. 19, 2017

(65) Prior Publication Data
US 2019/0021889 A1    Jan. 24, 2019

(51) Int. Cl.
| A61F 2/915 | (2013.01) |
| A61F 2/89 | (2013.01) |
| A61F 2/958 | (2013.01) |
| A61F 2/82 | (2013.01) |

(52) U.S. Cl.
CPC .............. *A61F 2/89* (2013.01); *A61F 2/915* (2013.01); *A61F 2/958* (2013.01); *A61F 2002/825* (2013.01); *A61F 2002/91508* (2013.01); *A61F 2002/91558* (2013.01); *A61F 2002/91583* (2013.01); *A61F 2210/0014* (2013.01); *A61F 2230/006* (2013.01); *A61F 2230/0013* (2013.01); *A61F 2230/0056* (2013.01); *A61F 2230/0069* (2013.01); *A61F 2250/0067* (2013.01)

(58) Field of Classification Search
CPC ....................... A61F 2/915; A61F 2002/91508
See application file for complete search history.

(56) References Cited

U.S. PATENT DOCUMENTS

| 4,580,568 A | 4/1986 | Gianturco et al. |
| 4,931,615 A | 6/1990 | Muncy et al. |
| 5,102,417 A | 4/1992 | Palmaz et al. |
| 5,104,404 A | 4/1992 | Wolff et al. |
| 5,292,331 A | 3/1994 | Boneau et al. |
| 5,449,373 A | 9/1995 | Pinchasik et al. |
| 5,607,442 A | 3/1997 | Fischell et al. |
| 5,632,771 A | 5/1997 | Boatman et al. |

(Continued)

FOREIGN PATENT DOCUMENTS

| JP | 1999505441 | 5/1999 |
| JP | 2000316983 A | 11/2000 |

(Continued)

*Primary Examiner* — Suba Ganesan
(74) *Attorney, Agent, or Firm* — Fulwider Patton LLP

(57) ABSTRACT

The invention is directed to an expandable stent for implanting in a body lumen, such as a coronary artery, peripheral artery, or other body lumen. The invention provides for an intravascular stent having a plurality of cylindrical rings connected by undulating links. The stent has a high degree of flexibility in the longitudinal direction, yet has adequate vessel wall coverage and sufficient radial strength to hold open an artery or other body lumen. The stent can be compressed or crimped onto a catheter to a very low profile since the inside radii of curvature of some of the peaks and valleys allow the stent to be crimped to a very low profile onto a catheter and increase radial strength over prior art stents.

20 Claims, 8 Drawing Sheets

(56) References Cited

U.S. PATENT DOCUMENTS

| | | |
|---|---|---|
| 5,643,312 A | 7/1997 | Fischell et al. |
| 5,669,932 A | 9/1997 | Fischell et al. |
| 5,674,241 A | 10/1997 | Bley et al. |
| 5,674,278 A | 10/1997 | Boneau et al. |
| 5,697,971 A | 12/1997 | Fischell et al. |
| 5,733,303 A | 3/1998 | Israel et al. |
| 5,741,327 A | 4/1998 | Frantzen et al. |
| 5,755,781 A | 5/1998 | Jayaraman et al. |
| 5,776,161 A | 7/1998 | Globerman et al. |
| 5,807,404 A | 9/1998 | Richter et al. |
| 5,810,872 A | 9/1998 | Kanesaka et al. |
| 5,824,040 A | 10/1998 | Cox et al. |
| 5,827,321 A | 10/1998 | Roubin et al. |
| 5,836,964 A | 11/1998 | Richter et al. |
| 5,843,120 A | 12/1998 | Israel et al. |
| 5,843,175 A | 12/1998 | Frantzen et al. |
| 5,853,419 A | 12/1998 | Imran et al. |
| 5,868,781 A | 2/1999 | Killion et al. |
| 5,868,783 A | 2/1999 | Tower et al. |
| 5,876,449 A | 3/1999 | Starck et al. |
| 5,879,370 A | 3/1999 | Fischell et al. |
| 5,879,382 A | 3/1999 | Boneau et al. |
| 5,893,887 A | 4/1999 | Jayaraman et al. |
| 5,911,754 A | 6/1999 | Kanesaka et al. |
| 5,913,895 A | 6/1999 | Burpee et al. |
| 5,922,005 A | 7/1999 | Richter et al. |
| 5,922,020 A | 7/1999 | Klein et al. |
| 5,925,061 A | 7/1999 | Ogi et al. |
| 5,931,866 A | 8/1999 | Frantzen et al. |
| 5,935,162 A | 8/1999 | Dang et al. |
| 5,938,682 A | 8/1999 | Hojeibane et al. |
| 5,938,697 A | 8/1999 | Killion et al. |
| 5,948,016 A | 9/1999 | Jang et al. |
| 5,954,743 A | 9/1999 | Jang et al. |
| 5,964,798 A | 10/1999 | Imran et al. |
| 5,967,986 A | 10/1999 | Cimochowski et al. |
| 5,968,093 A | 10/1999 | Kranz et al. |
| 5,972,018 A | 10/1999 | Israel et al. |
| 5,980,552 A | 11/1999 | Pinchasik et al. |
| 5,992,000 A | 11/1999 | Humphrey et al. |
| 5,993,489 A | 11/1999 | Lewis et al. |
| 6,001,125 A | 12/1999 | Golds et al. |
| 6,004,348 A | 12/1999 | Banas et al. |
| 6,013,091 A | 1/2000 | Ley et al. |
| 6,017,365 A | 1/2000 | Von Oepen et al. |
| 6,019,789 A | 2/2000 | Dinh et al. |
| 6,022,371 A | 2/2000 | Killion et al. |
| 6,022,374 A | 2/2000 | Imran et al. |
| 6,027,526 A | 2/2000 | Limon et al. |
| 6,033,433 A | 3/2000 | Ehr et al. |
| 6,033,435 A | 3/2000 | Penn et al. |
| 6,039,755 A | 3/2000 | Edwin et al. |
| 6,039,756 A | 3/2000 | Jang et al. |
| 6,042,597 A | 3/2000 | Kveen et al. |
| 6,042,606 A | 3/2000 | Frantzen et al. |
| 6,048,361 A | 4/2000 | Von Oepen et al. |
| 6,051,020 A | 4/2000 | Goicoechea et al. |
| 6,053,940 A | 4/2000 | Wijay et al. |
| 6,053,941 A | 4/2000 | Lindenberg et al. |
| 6,053,943 A | 4/2000 | Edwin et al. |
| 6,056,775 A | 5/2000 | Borghi et al. |
| 6,056,776 A | 5/2000 | Lau et al. |
| 6,059,822 A | 5/2000 | Kanesaka et al. |
| 6,063,113 A | 5/2000 | Kavteladze et al. |
| 6,066,168 A | 5/2000 | Lau et al. |
| 6,066,169 A | 5/2000 | McGuinness et al. |
| 6,068,656 A | 5/2000 | Von Oepen et al. |
| 6,071,298 A | 6/2000 | Lashinski et al. |
| 6,077,297 A | 6/2000 | Robinson et al. |
| 6,080,191 A | 6/2000 | Summers et al. |
| 6,083,259 A | 7/2000 | Frantzen et al. |
| 6,086,604 A | 7/2000 | Fischell et al. |
| 6,086,611 A | 7/2000 | Duffy et al. |
| 6,090,127 A | 7/2000 | Globerman et al. |
| 6,093,199 A | 7/2000 | Brown et al. |
| 6,093,203 A | 7/2000 | Uflacker et al. |
| 6,099,455 A | 8/2000 | Columbo et al. |
| 6,099,559 A | 8/2000 | Nolting et al. |
| 6,099,560 A | 8/2000 | Penn et al. |
| 6,099,561 A | 8/2000 | Alt et al. |
| 6,102,940 A | 8/2000 | Robichon et al. |
| 6,106,548 A | 8/2000 | Roubin et al. |
| 6,108,886 A | 8/2000 | Kimes et al. |
| 6,113,627 A | 9/2000 | Jang et al. |
| 6,113,628 A | 9/2000 | Borghi et al. |
| 6,117,165 A | 9/2000 | Becker et al. |
| 6,123,721 A | 9/2000 | Jang et al. |
| 6,129,754 A | 10/2000 | Kanesaka et al. |
| 6,129,755 A | 10/2000 | Mathis et al. |
| 6,149,682 A | 11/2000 | Frid et al. |
| 6,152,957 A | 11/2000 | Jang et al. |
| 6,156,052 A | 12/2000 | Richter et al. |
| 6,162,243 A | 12/2000 | Gray et al. |
| 6,179,868 B1 | 1/2001 | Burpee et al. |
| 6,183,506 B1 | 2/2001 | Penn et al. |
| 6,187,034 B1 | 2/2001 | Frantzen |
| 6,190,403 B1 | 2/2001 | Fischell et al. |
| 6,200,334 B1 | 3/2001 | Jang |
| 6,206,916 B1 | 3/2001 | Furst |
| 6,217,608 B1 | 4/2001 | Penn et al. |
| 6,241,762 B1 | 6/2001 | Shanley |
| 6,258,116 B1 | 7/2001 | Hojeibane |
| 6,264,688 B1 | 7/2001 | Herklotz et al. |
| 6,309,414 B1 | 10/2001 | Rolando et al. |
| 6,325,821 B1 | 12/2001 | Gaschino et al. |
| 6,325,826 B1 | 12/2001 | Vardi et al. |
| 6,330,884 B1 | 12/2001 | Kim |
| 6,342,067 B1 | 1/2002 | Mathis et al. |
| 6,348,065 B1 | 2/2002 | Brown et al. |
| 6,375,677 B1 | 4/2002 | Penn et al. |
| 6,416,539 B1 | 7/2002 | Hassdenteufel |
| 6,451,049 B2 | 9/2002 | Vallana et al. |
| 6,497,723 B1 | 12/2002 | Starck et al. |
| 6,540,775 B1 | 4/2003 | Fischell et al. |
| 6,602,281 B1 | 8/2003 | Klein |
| 6,610,086 B1 | 8/2003 | Kock et al. |
| 6,613,081 B2 | 9/2003 | Kim et al. |
| 6,616,689 B1 | 9/2003 | Ainsworth et al. |
| 6,618,921 B1 | 9/2003 | Thornton |
| 6,626,935 B1 | 9/2003 | Ainsworth et al. |
| 6,629,994 B2 | 10/2003 | Gomez et al. |
| 6,656,220 B1 | 12/2003 | Gomez et al. |
| 6,669,722 B2 | 12/2003 | Chen et al. |
| 6,730,116 B1 | 5/2004 | Wolinsky et al. |
| 6,740,114 B2 | 5/2004 | Burgermeister |
| 6,805,707 B1 | 10/2004 | Hong et al. |
| 6,929,657 B2 | 8/2005 | Gomez et al. |
| 6,942,689 B2 | 9/2005 | Majercak |
| 6,969,373 B2 | 11/2005 | Schwartz et al. |
| 6,998,060 B2 | 2/2006 | Tomonto |
| 7,204,848 B1 | 4/2007 | Brown et al. |
| 2003/0040790 A1 | 2/2003 | Furst |
| 2003/0195606 A1 | 10/2003 | Davidson et al. |
| 2004/0230293 A1* | 11/2004 | Yip .......... A61F 2/915 623/1.16 |
| 2007/0005123 A1* | 1/2007 | Sano .......... A61F 2/91 623/1.15 |

FOREIGN PATENT DOCUMENTS

| | | |
|---|---|---|
| JP | 2001112873 A | 4/2001 |
| WO | 9822159 A2 | 5/1998 |
| WO | 9902105 A1 | 1/1999 |
| WO | 0030563 A1 | 6/2000 |
| WO | 0042945 A1 | 7/2000 |
| WO | 0100112 A1 | 1/2001 |

* cited by examiner

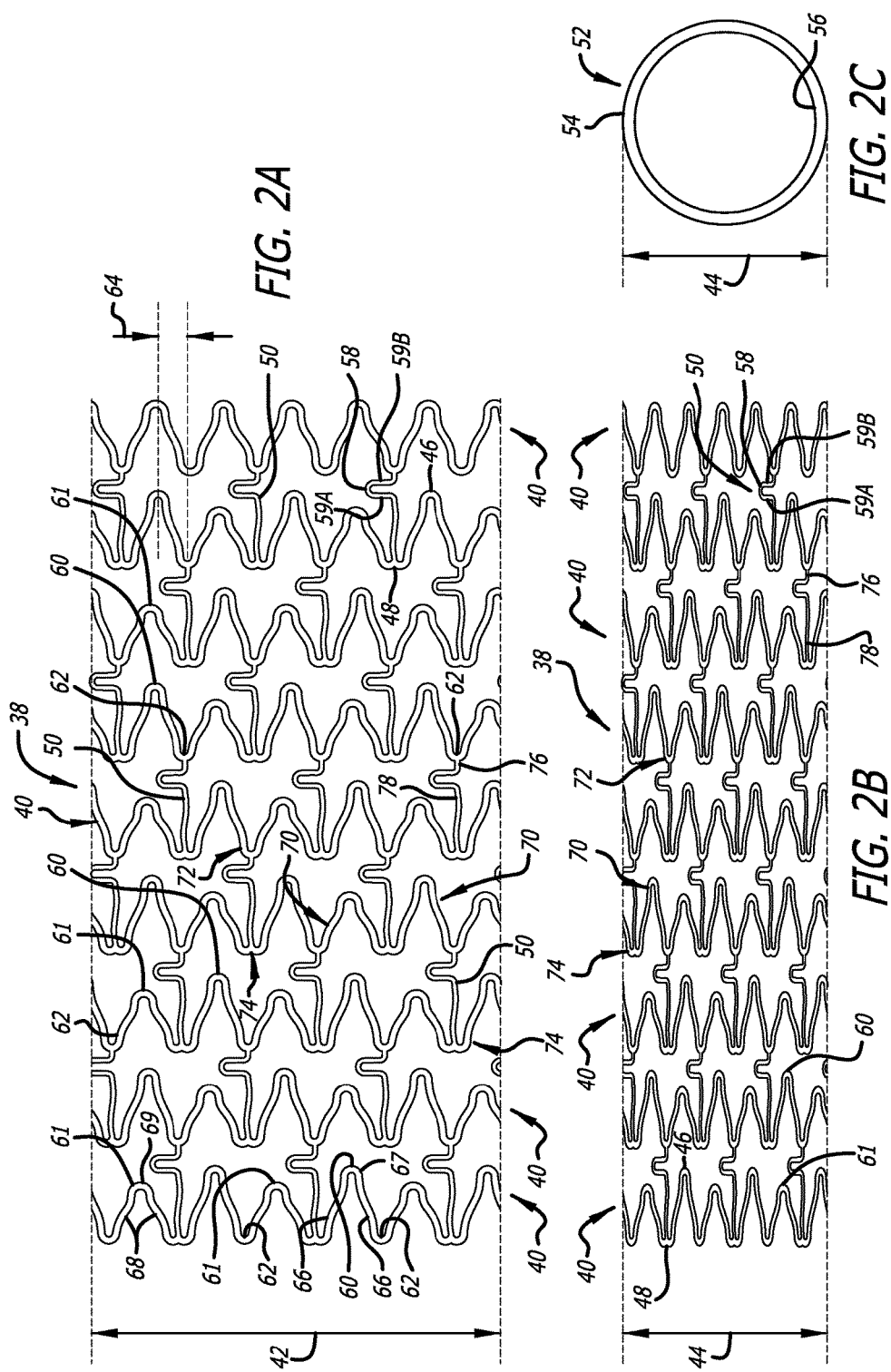

INTRAVASCULAR STENT

BACKGROUND

The invention relates to vascular repair devices, in particular intravascular stents, which are adapted to be implanted in a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, the prior art stents depicted in FIGS. 1A-1C have multiplex cylindrical rings connected by one or more undulating links. While some of these stents are flexible and have the appropriate radial rigidity needed to hold open a vessel or an artery, there typically is a tradeoff between flexibility and radial strength and the ability of the stent to be tightly compressed or crimped onto a catheter so that it does not move relative to the catheter or dislodge prematurely prior to controlled implantation in a vessel.

What has been needed and heretofore unavailable is a stent which has a high degree of flexibility so that it can be advanced through tortuous passageways and can be readily expanded at the treatment site, and yet has the mechanical strength to hold open the body lumen or artery in which it is implanted and provide adequate vessel wall coverage. The present invention satisfies this need. That is, the stent of the present invention has a high degree of compressibility to secure itself on the catheter and provide a low profile and a high degree of flexibility making it possible to advance the stent easily through tortuous arteries, yet the stent has sufficient radial rigidity so that it can hold open an artery or other blood vessel or tack up a dissected lining and provide adequate vessel wall coverage.

SUMMARY OF THE INVENTION

The present invention is directed to an intravascular stent that has a pattern or configuration that permits the stent to be tightly compressed or crimped onto a catheter to provide an extremely low profile and to prevent relative movement between the stent and the catheter. The stent also is highly flexible along its longitudinal axis to facilitate delivery through tortuous body lumens, but it is stiff and stable enough radially in its expanded condition to maintain the patency of a body lumen such as an artery when the stent is implanted therein. In other words, the stent of the present invention can be crimped tightly to a very low profile onto a balloon catheter and provides flexibility along its longitudinal axis, yet maintaining very high radial strength when expanded to the implanted diameter in a vessel.

The stent of the present invention generally includes a plurality of cylindrical rings that are interconnected to form the stent. The stent typically is mounted on a balloon catheter if it is balloon expandable or mounted on or in a catheter without a balloon if it is self-expanding.

Each of the cylindrical rings making up the stent has a proximal end and a distal end and a cylindrical plane defined by a cylindrical outer wall surface that extends circumferentially between the proximal end and the distal end of the cylindrical ring. Generally, the cylindrical rings have a serpentine or undulating shape which includes at least one U-shaped element, and typically each ring has more than one U-shaped element. The cylindrical rings are interconnected by at least one undulating link which attaches one cylindrical ring to an adjacent cylindrical ring. The undulating links are highly flexible and allow the stent to be highly flexible along its longitudinal axis. At least some of the undulating links have a curved portion that extends transverse to the stent longitudinal axis for a predetermined distance that coincides with one of the U-shaped elements. More specifically, the curved portion extends in a transverse manner such that it would intersect with the corresponding U-shaped element, however the corresponding U-shaped element is shorter in length than other U-shaped elements in the same ring. Thus, when the stent is compressed or crimped onto the catheter, the curved portion of the link does not overlap or intersect with the adjacent U-shaped element since that element is shorter in length than similar U-shaped elements in the particular ring. In this manner, the stent can be compressed or crimped to a much tighter or smaller diameter onto the catheter which permits low profile delivery as well as a tight gripping force on the catheter to reduce the likelihood of movement between the stent and the catheter during delivery and prior to implanting the stent in the vessel.

The undulating links may take various configurations but in general have an undulating or serpentine shape. The undulating links can include bends connected by straight portions wherein the straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent is bent in any direction along its longitudinal axis. Uniform flexibility along the stent derives in part from the links of one ring being circumferentially offset from the links in an adjacent ring. Further, the cylindrical rings are configured to provide flexibility to the stent in that portions of the rings can flex or bend as the stent is delivered through a tortuous vessel.

The cylindrical rings typically are formed of a plurality of peaks and valleys, where the valleys of one cylindrical ring are circumferentially aligned to the valleys of an adjacent cylindrical ring. In this configuration, at least one undulating link attaches each cylindrical ring to an adjacent cylindrical ring so that at least a portion of the undulating links is positioned within one of the valleys, and it attaches the valley to an adjacent valley.

While the cylindrical rings and undulating links generally are not separate structures, they have been conveniently referred to as rings and links for ease of identification. Further, the distal side of the cylindrical rings can be thought of as comprising of a series of U's, W's and Y-shaped structures in a repeating pattern while the proximal cylindrical ring is comprised of all U-shaped elements. Again, while the cylindrical rings are not divided up or segmented into U's, W's and Y's, the pattern of the cylindrical rings resemble such configurations. The U's, W's and Y's promote flexibility in the stent primarily by flexing as the stent is delivered through a tortuous vessel.

The undulating links are positioned so that the curved portion of the link is outside the curved part of the W-shaped portion. Since the curved portion does not substantially expand (if at all) when the stent is expanded, it will continue to provide good vessel wall coverage even as the curved part of the W-shaped portion spreads apart as the stent is expanded. The curved portion of the link extends in a direction transverse to the stent longitudinal axis for a distance that positions it adjacent and proximal to the peak of a U-shaped element. These U-shaped elements have struts that are shorter than the struts of the other U-shaped elements in the same cylindrical ring so that as the stent is compressed, the curved portion of the link does not overlap the adjacent U-shaped element even though the curved portion of the link and the U-shaped element are aligned along the stent longitudinal axis.

In one embodiment, the inner radii of some or all of the U-shaped portions, the Y-shaped portions, and the W-shaped portions are smaller than prior art stents and preferably no greater than 0.002677 inch (68 micron) on the distal end ring and no greater than 0.001969 inch (50 micron) on the body rings and proximal end ring. The reduced radii provide a stent that can be crimped to a very low profile onto a balloon catheter, yet providing increased radial strength when the stent is expanded to the implanted diameter.

In another embodiment, the undulating links have a first arm and a second arm for connecting the undulating links to adjacent cylindrical rings. Some or all of the first arms have multiple slight bends along the length to reduce the likelihood of adjacent bar arms swinging toward the link during compression and expansion. The result is a straighter crimped stent and a straighter expanded stent. The number and location of undulating links that interconnect adjacent cylindrical rings can be varied as the application requires. Since the undulating links typically do not expand when the cylindrical rings of the stent expand radially outwardly, the links are free to continue to provide flexibility and to also provide a scaffolding function to assist in holding open the vessel or artery. Importantly, the addition or removal of the undulating links has very little impact on the overall longitudinal flexibility of the stent. Each undulating link is configured so that it promotes flexibility whereas some prior art connectors actually reduce flexibility of the stent.

The cylindrical rings of a metallic balloon expandable stent are plastically deformed when expanded beyond the yield stress. Typically, metallic balloon-expandable stents are made from a stainless steel alloy, cobalt-chromium alloy, titanium, or similar materials.

Similarly, the cylindrical rings of a stent expand radially outwardly when the stent is formed from superelastic alloys, such as nickel-titanium (NiTi) alloys. In the case of superelastic alloys, the stent expands upon application of a temperature change or when a stress is relieved, as in the case of a pseudoelastic phase change.

Because of the undulating configuration of the links, the stent has a high degree of flexibility along its axis, which reduces the tendency for stent fishscaling (i.e., flaring). Stent fishscaling can occur when a stent is deployed in a curved artery or blood vessel, and portions of the stent project outward. The present invention undulating links reduce the likelihood of fishscaling.

Further, because of the positioning of the links and the fact that the links do not expand or stretch significantly when the stent is radially expanded, the overall length of the stent is substantially the same in the unexpanded and expanded configurations. In other words, the stent will not substantially shorten upon expansion.

The stent may be formed from a tube by laser cutting the pattern of cylindrical rings and undulating links in the tube. The stent also may be formed by laser cutting a flat metal sheet in the pattern of the cylindrical rings and links, and then rolling the pattern into the shape of the tubular stent and providing a longitudinal weld to form the stent.

BRIEF DESCRIPTION OF THE DRAWINGS

FIG. 2A is a plan view of one embodiment of an expanded tubular stent which illustrates the pattern of the cylindrical rings and undulating links.

FIG. 2B is a plan view of the tubular stent of FIG. 2A which illustrates the pattern of the cylindrical rings and undulating links in a crimped configuration.

FIG. 2C is an end view of the tubular stent of FIG. 2B depicting the cylindrical plane of the stent.

DETAILED DESCRIPTION OF THE PREFERRED EMBODIMENTS

The present invention stent improves on existing stents by providing a longitudinally flexible stent having a uniquely designed pattern and novel interconnecting members. In addition to providing longitudinal flexibility, the stent of the present invention also provides radial rigidity and a high degree of scaffolding of a vessel wall, such as a coronary artery. The design of the highly flexible interconnecting members and their placement relatively to an adjacent U-shaped member provides for a tightly compressed stent onto a catheter while maintaining a high degree of flexibility during delivery.

One of the problems associated with some prior art stents is the ability to be more tightly crimped or compressed onto the balloon portion of the catheter. Preferably, the undulating portion of a link and the adjacent struts should not overlap, therefore the undulating portion of the link limits the amount of crimping or compression of each cylindrical ring onto the balloon portion of the catheter. The present invention solves this problem and allows for a tightly compressed or crimped stent onto the catheter.

Figure 1A:
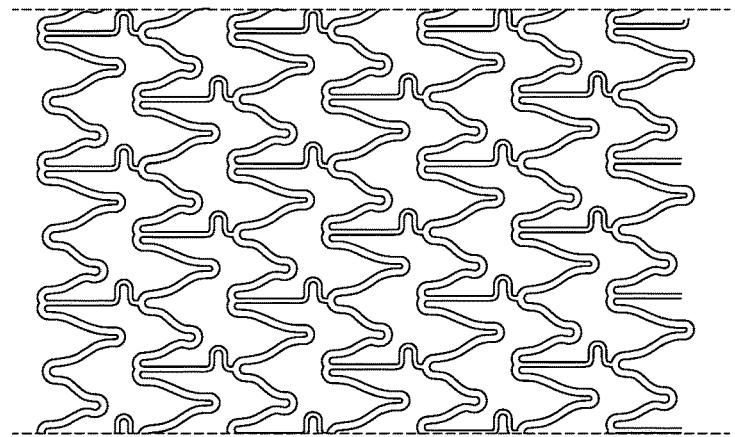
FIG. 1A is a plan view of a prior art flattened stent of one embodiment of the invention which illustrates the pattern of rings and links.
Figure 1B:
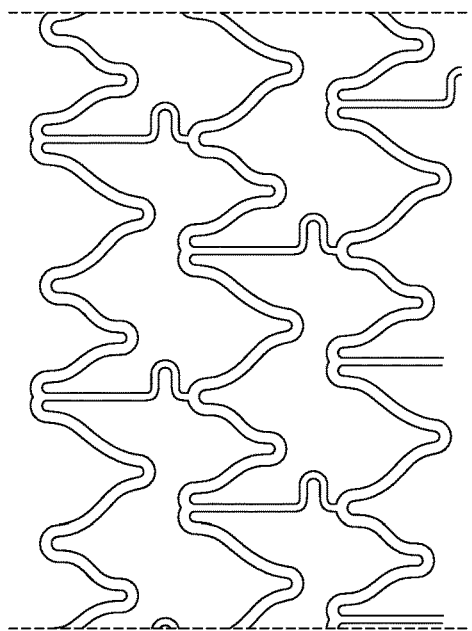
FIG. 1B is a partial plan view of the prior art stent of FIG. 1A which has been expanded to an implanted diameter.
Figure 1C:
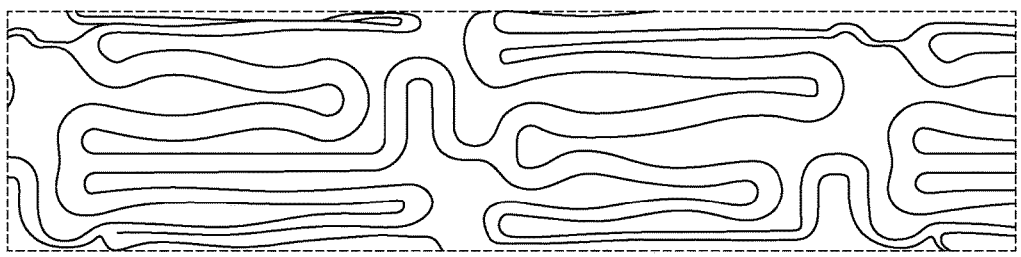
FIG. 1C is a plan view of a portion of the prior art stent of FIG. 1A rolled into a cylindrical configuration and tightly crimped so that the various stent struts are either in close contact or contacting each other.

FIGS. 1A-1C depict a prior art stent in various configurations. Referring to FIG. 1A, the stent is shown in a flattened condition so that the pattern can be clearly viewed, even though the stent is in a cylindrical form when in use, such as shown in FIG. 1C. The stent is typically formed from a tubular member, however it can be formed from a flat sheet such as shown in FIG. 1A and rolled into a cylindrical configuration as shown in FIG. 1C.

In keeping with the invention and as shown in FIGS. 2A-8, stent 38 is made up of a plurality of cylindrical rings 40 which extend circumferentially around the stent when it is in a tubular form. The stent has an implanted diameter 42 as shown in FIG. 2A and a delivery diameter 44 as shown in FIG. 2B. The delivery diameter 44 represents how tightly the stent can be crimped onto the balloon of a delivery catheter, and for a small diameter stent, the minimum crimp profile or diameter can be as small as 0.0297 inch (0.754 mm). The stent shown in FIG. 2B generally would be more tightly crimped or compressed for delivery in a vessel, however, it is easier to see and describe the component parts in this view. Each cylindrical ring 40 has a proximal end 46 and a distal end 48. The cylindrical rings 40 are connected to each other by undulating links 50. Typically, since the stent is laser cut from a tube, there are no discreet parts such as the described cylindrical rings and links, however it is beneficial for identification and reference to various parts to refer to the cylindrical rings and links and other parts of the stent as follows.

As shown most clearly in FIG. 2C, each cylindrical ring 40 defines a cylindrical plane 52 which is a plane defined by the proximal and distal ends 46,48 of the ring and the circumferential extent as the cylindrical ring travels around the cylinder. Each cylindrical ring includes a cylindrical outer wall surface 54 which defines the outermost surface of the stent and a cylindrical inner wall surface 56 which defines the innermost surface of the stent. Cylindrical plane 52 follows the cylindrical outer wall surface.

In keeping with the invention, undulating link 50 is positioned within cylindrical plane 52. The undulating links connect one cylindrical ring 40 to an adjacent cylindrical ring 40 and contribute to the overall longitudinal flexibility of the stent due to their unique construction. The flexibility of the undulating links derives in part from curved portion 58 connected to straight portions 59A and 59B, wherein the straight portions are substantially perpendicular to the longitudinal axis of the stent. Thus, as the stent is being delivered through a tortuous vessel, such as a coronary artery, the curved portions 58 and straight portions 59A and 59B of the undulating links will permit the stent to flex in the longitudinal direction (like a hinge) which significantly enhances delivery of the stent to the target treatment site. The number of bends and straight portions in a link can be increased or decreased from that shown to achieve differing flexibility constructions. With the straight portions being substantially perpendicular to the stent longitudinal axis, the undulating link acts much like a hinge at the curved portion 58 to provide flexibility. A straight link that is parallel to the stent axis typically is not flexible and does not add to the flexibility of the stent.

Referring to FIGS. 2A-8, the stent 38 can be described more particularly as having a plurality of first peaks 60, second peaks 61, and valleys 62. Although the stent is not divided into separate elements, for ease of discussion, references to peaks and valleys is appropriate. The number of peaks and valleys can vary for each ring depending upon the application. Thus, for example, if the stent is to be implanted in a coronary artery, a lesser number of peaks and valleys are required than if the stent is implanted in a peripheral artery, which has a larger diameter than a coronary artery. As can be seen, for example, in FIG. 3, peaks 60,61 are in phase, meaning that the peaks 60,61 point in the same direction and are substantially aligned along the longitudinal axis of the stent. It may be desirable under certain circumstances to position the peaks so that they are out of phase (not shown), that is, the peaks of one ring would be circumferentially offset from the peaks of an adjacent ring so that the apex of adjacent peaks pointed toward each other. As shown in FIGS. 2A-8, the peaks are circumferentially offset 64 from the valleys and from the undulating link 50. Positioning the peaks, valleys, and undulating links in this manner provides a stent having uniform expansion capability, high radial strength, a high degree of flexibility, and sufficient wall coverage to support the vessel.

In keeping with the invention, and as shown in FIGS. 2A-8, a small diameter stent has a maximum nominal implanted diameter 44 of 0.1575 inch (4.0 mm). For the small diameter stent, each of the cylindrical rings has a plurality of first peaks 60 which have first bar arms 66 attached to a first apex 67. The first struts can be either curved or straight depending upon the particular application. The cylindrical rings also have second peaks 61 which have second bar arms 68 attached to a second apex 69. Again, the second bar arms can be either curved or straight depending upon the particular application. Importantly, the length of the first bar arms 66 are longer than the length of the second bar arms 68. As can be seen in FIG. 2B, when the stent is in a crimped condition, or a partially crimped condition, the first bar arms and second bar arms respectively will be closer to each other when the stent is compressed or crimped onto the balloon or expandable member of the catheter. The crimping or compressing process, however, also moves the undulating link 50 along with its curved portion 58 closer to the second peak 61. In order to allow the stent to be more tightly crimped onto the balloon portion of the catheter and to avoid overlapping between the undulating link 50 and the second peak 61, the second bar arms 68 are shorter than the first bar arms 66, thus avoiding any overlapping contact between the curved portion 58 of the undulating link 50 and the second peak 61. The various stent bar arms, curved portions, links, and peaks and valleys may contact each other when the stent is crimped or compressed, but overlapping is an undesirable feature.

More particularly, in order to more tightly crimp or compress the cylindrical rings 40 of the stent 38, the undulating link 50 is tightly crimped or compressed into near contact with second peak 61. As can be seen for example, in FIGS. 2A-8, curved portion 58 and straight portions 59A and 59B are in close relation to second peak 61 and in near contact with second apex 69. The curved portion 58 of the link is proximal to the second peak 61, and the first and second bar arms 66,69 in each of the rings are tightly compressed to be in near contact with each other. For example, first bar arms 66 and second bar arms 68 as well as arm 78 of the undulating link all are in close contact with each other in order to provide a very low crimp profile, tightly crimped stent onto the balloon portion of the catheter. Likewise, if the stent is formed of a self-expanding material such as nickel-titanium, the stent will similarly be tightly crimped and positioned within a sheath or within the catheter for delivery in the vascular system. Importantly, the curved portion and the straight portions of the undulating link are positioned relative to the second peak to allow the stent to be tightly crimped as described.

Referring to FIGS. 2A-8, the stent 38 of the invention also can be described as having cylindrical rings formed of U-shaped portions 70, Y-shaped portions 72, and W-shaped portions 74. Again, while the stent is generally laser cut from a tube and it typically has no discreet parts, for ease of identification, the stent of the invention also can be referred to as having U-, Y-, and W-shaped portions. The U-shaped portions 70 have no supporting structure attached thereto. The Y-shaped portions 72, at their base or apex, have arm 76 extending therefrom which is attached to undulating link 50. The W-shaped portion 74 has at its base or curve portion an arm 78 which attaches at the other end of the undulating link. The lengths of the arms attaching the link to the rings can vary.

Figure 3:
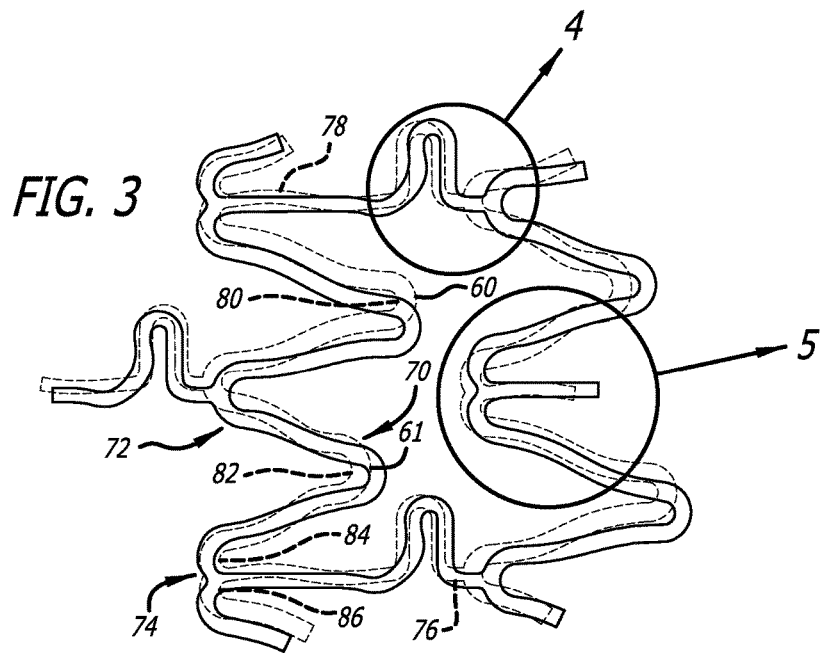
FIG. 3 is a plan view of a portion of a flattened configuration of the expanded tubular stent of FIG. 2A.
Figure 4:
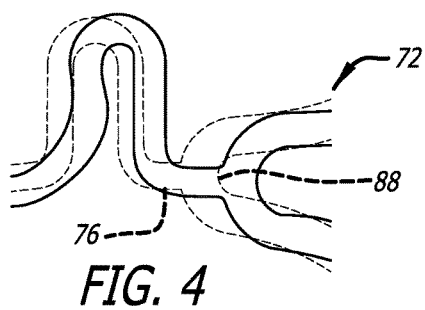
FIG. 4 is a plan view of a portion of the stent of FIG. 3 depicting the reduced inner radii in some valleys and increased strut widths in some bar arms.
Figure 5:
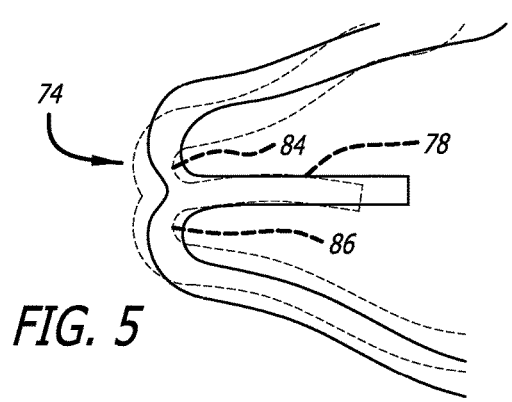
FIG. 5 is an enlarged plan view of a portion of the stent of FIG. 3.
Figure 8:
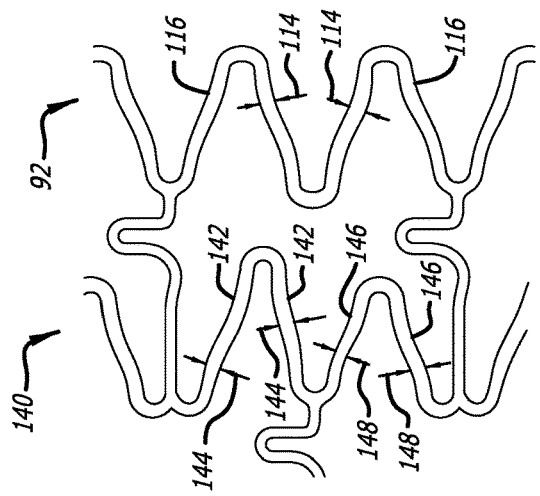
FIG. 8 is a plan view of a portion of the stent of FIG. 2A depicting the strut widths of the bar arms and peaks of the proximal end ring and the adjacent ring or second to proximal end ring.
Figure 7:
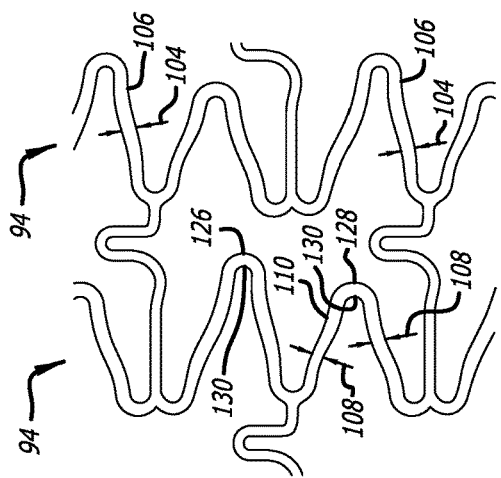
FIG. 7 is a plan view of a portion of the stent of FIG. 2A depicting the strut widths of the bar arms and peaks of the body rings.
Figure 6:
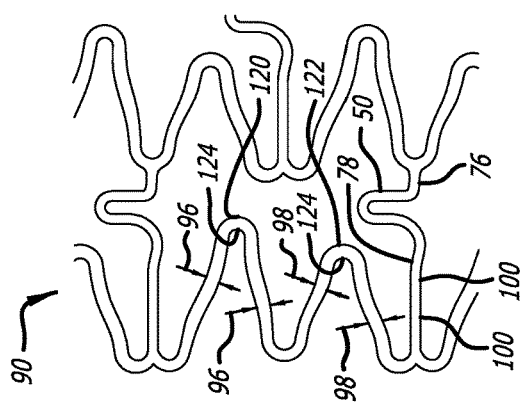
FIG. 6 is a plan view of a portion of the stent of FIG. 2A depicting the strut widths of the bar arms and peaks of the distal end ring.
Figure 9A:
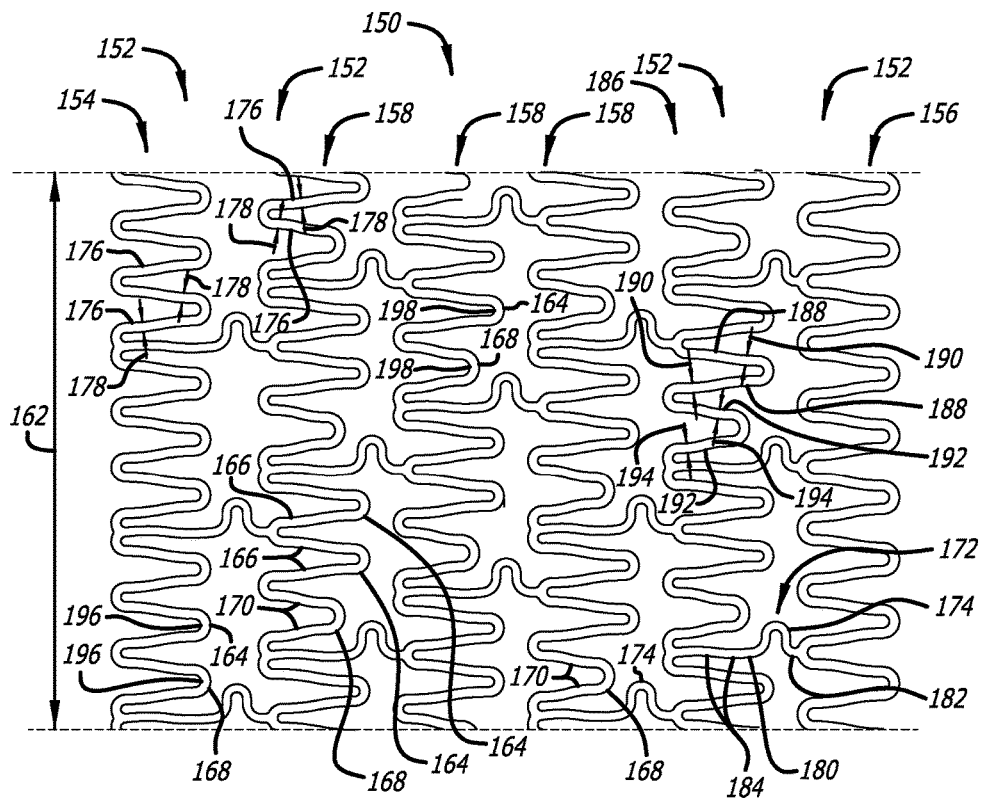
FIG. 9A is a plan view of one embodiment of an expanded tubular stent which illustrates the pattern of the cylindrical rings and undulating links.
Figure 9B:
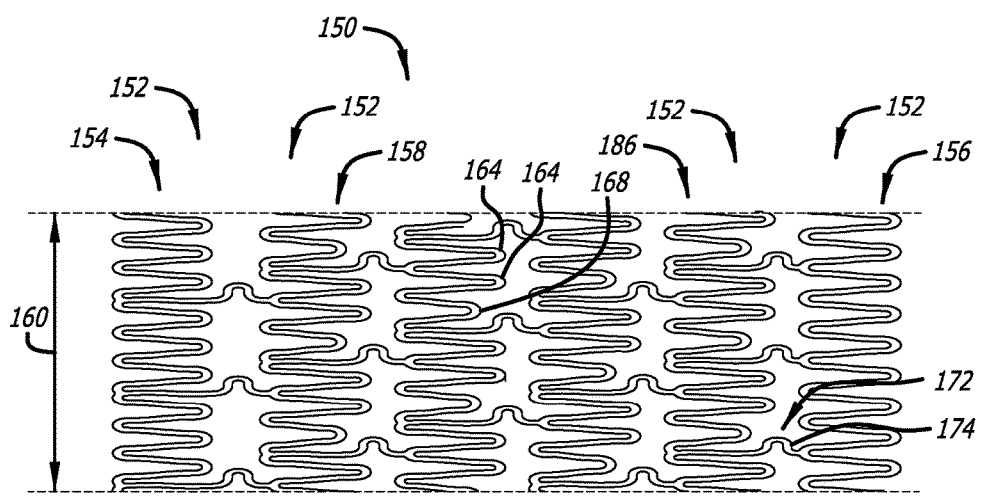
FIG. 9B is a plan view of the tubular stent of FIG. 9A which illustrates the pattern of the cylindrical rings and undulating links in a crimped configuration.
Figure 10:
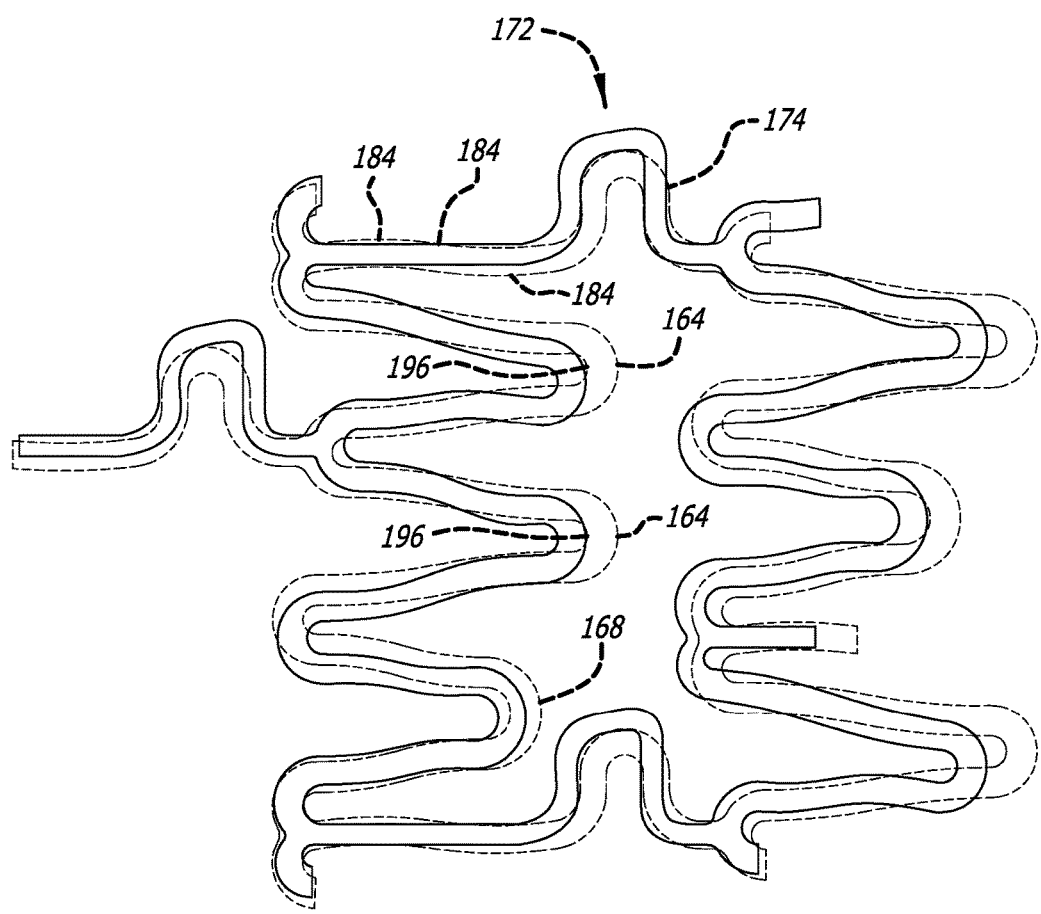
FIG. 10 is a plan view of a portion of the stent of FIG. 9A depicting the reduced inner radii in some peaks and valleys and increased strut widths in some bar arms.
Figure 13:
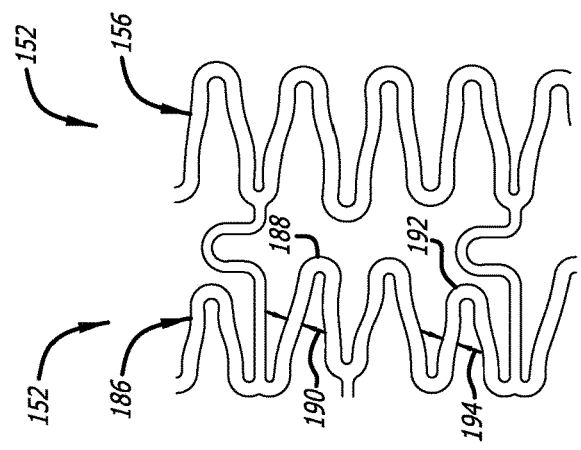
FIG. 13 is a plan view of a portion of the stent of FIG. 9A depicting strut widths of the bar arms and peaks of the proximal end ring and the adjacent ring or second to proximal end ring.
Figure 12:
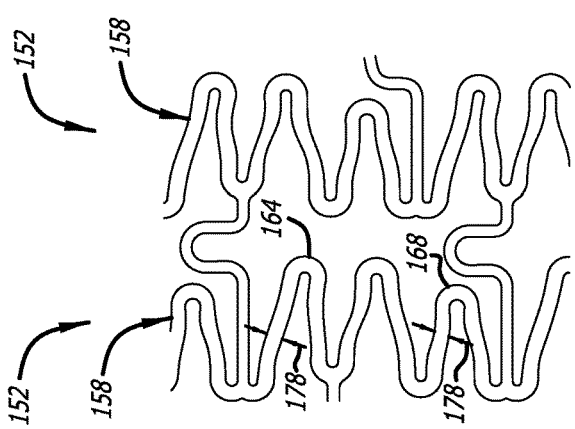
FIG. 12 is a plan view of a portion of the stent of FIG. 9A depicting the strut widths of the bar arms and peaks of the body rings.
Figure 11:
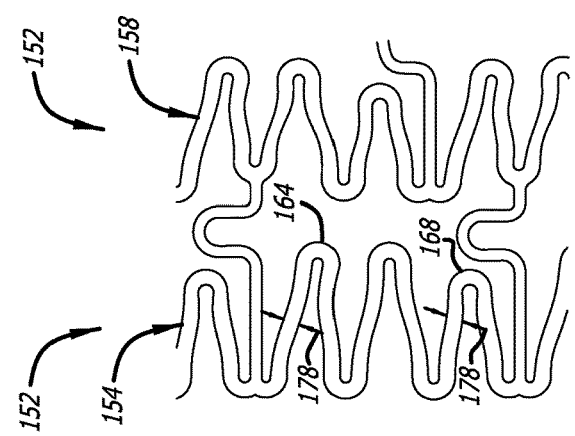
FIG. 11 is a plan view of a portion of the stent of FIG. 9A depicting the strut widths of the bar arms and peaks of the distal end ring.

Due to the intricate patterns as disclosed in FIGS. 3-5, the rate of expansion of the various portions of the stent, including the U-shaped portion 70, the Y-shaped portion 72, and the W-shaped portion 74, can vary. The solid lines shown in FIGS. 3-5 are prior art stent designs, while the dashed lines show critical changes in the inner radii of structural members to allow the stent to expand evenly and maintain high radial strength. Accordingly, one aspect of the invention provides for different radii of curvature at various points so that the stent will expand evenly and uniformly. Thus, first radius 80 which corresponds with first peak 60 has a smaller radius of curvature than does second radius 82 which corresponds with second peak 61. Generally, the longer the struts associated with a peak, the more easily that portion of the stent will expand, so that a smaller radius is associated with peaks having longer struts. Likewise, for peaks, such as second peak 61, which has second bar arms 68 that are shorter than the first bar arms 66 of first peak 60, has a greater radius of curvature which will expand more easily in order to compensate for the stiffer bending moments created by the shorter second bar arms 68.

Also referring to FIGS. 3-5, the radius of curvature of the various portions of the W-shaped portion also varies to provide uniform stent expansion. Since the second peak 61 and its associated second bar arms 68 have a tendency to expand more slowly as the stent is expanded, a greater radius of a curvature is provided in the adjacent part of the W-shaped portion 74. Thus, third radius 84 of the W-shaped portion 74 is greater than the fourth radius 86 in the W-shaped portion. The third radius 84 is adjacent to second peak 61 which has a tendency to expand more slowly, while the fourth radius 86 is adjacent the first peak 60 which has a tendency to expand more easily. By varying the radii of curvature in the W-shaped portion, the stent will expand more evenly and compensate for the varying rates of expansion of adjacent portions in a cylindrical ring. A fifth radius 88 corresponds to the inner radius of the Y-shaped portion 72.

In one embodiment as shown in FIGS. 2A, 2B and 6-8, a flexible intravascular stent 38 for use in a body lumen comprises a plurality of cylindrical rings 40 having a distal end cylindrical ring 90, a proximal end cylindrical ring 92, and a plurality of body cylindrical rings 94, all of the cylindrical rings being aligned along a common longitudinal axis and interconnected to form the stent. Each cylindrical ring has a delivery diameter 44 and an implanted diameter 42. Each cylindrical ring has a plurality of first peaks 60 connected by first bar arms 66 and second peaks 61 connected by second bar arms 68, each of the bar arms having a length, the second bar arms 68 being shorter than the first bar arms 66. At least one undulating link 50 attaches each cylindrical ring 40 to an adjacent cylindrical ring, the undulating links having a curved portion 58 extending transverse to the stent longitudinal axis toward the second peak 61, the height of the second peak 61 being sized so that as the stent is compressed to the delivery diameter 44, the curved portion 58 of the undulating link 50 is longitudinally aligned with and proximal to the second peak 61. The distal end cylindrical ring 90 has a first width 96 for the first bar arms 66 and a second width 98 for the second bar arms 68. Each undulating link 50 has long arm 78 and a short arm 76, the long arm 78 having multiple slight bends 100 along its length. The multiple slight bends 100 along the length of the long arm 78 help the undulating link 50 stay axially aligned and prevents swaying during crimping and expansion. The body cylindrical rings 94 have a third width 104 for a third set of bar arms 106 and a fourth width 108 for a fourth set of bar arms 110. The proximal end cylindrical ring 92 has a fifth bar arm width 114 for a fifth set of bar arms 116. The plurality of first peaks 120 and the plurality of second peaks 122 on the distal end cylindrical ring 90 have an inner radius 124 not to exceed 68 micron (0.0268 inch). The plurality of first peaks 126 and the plurality of second peaks 128 on the body cylindrical rings 94 have an inner radius 130 not to exceed 50 micron (0.00197 inch). Due to the improvements to the design of the inner radii 124 and 130, the delivery diameter 44 has been reduced to 0.754 mm (0.0297 inch).

In another embodiment, as shown in FIGS. 2A, 2B, and 6-8, a flexible intravascular stent 38 for use in a body lumen comprises a plurality of cylindrical rings 40 having a distal end cylindrical ring 90, a proximal end cylindrical ring 92, and a plurality of body cylindrical rings 94, all of the cylindrical rings being aligned along a common longitudinal axis and interconnected to form the stent. Each cylindrical ring has a first delivery diameter 44 and a second implanted diameter 42. Each cylindrical ring has a plurality of first peaks 60 connected by first bar arms 66 and second peaks 61 connected by second bar arms 68, each of the bar arms having a length, the second bar arms 68 being shorter than the first bar arms 66. At least one undulating link 50 attaches each cylindrical ring 40 to an adjacent cylindrical ring, the undulating links having a curved portion 58 extending transverse to the stent longitudinal axis toward the second peak 61, the height of the second peak 61 being sized so that as the stent is compressed to the delivery diameter 44, the curved portion 58 of the undulating link 50 is longitudinally aligned with and proximal to the second peak 61. The distal end cylindrical ring 90 and the plurality of body cylindrical rings 94 have bar arms of the same width. Each undulating link 50 has a long arm 78 and a short arm 76, the long arm 78 having multiple slight bends 100 along its length. The multiple slight bends 100 along the length of the long arm 78 help the undulating link 50 stay axially aligned and prevents swaying during crimping and expansion. The proximal end cylindrical ring 92 has bar arm widths that are greater than the bar arm widths of the distal end cylindrical ring 90 and the plurality of body cylindrical rings 94. A second to the proximal end cylindrical ring 140 (FIG. 8) has a sixth set of bar arms 142 having a sixth width 144 and a seventh set of bar arms 146 having seventh widths 148. The plurality of first peaks 120 and the plurality of second peaks 122 on the distal end cylindrical ring 90 have an inner radius 124 not to exceed 68 micron (0.0268 inch). The plurality of first peaks 126 and the plurality of second peaks 128 on the body cylindrical rings 94 have an inner radius 130 not to exceed 50 micron (0.00197 inch). Due to the improvements to the design of the inner radius 124 and 130, the delivery diameter 44 has been reduced to 0.754 mm (0.0297 inch).

In the embodiment shown in FIGS. 9A-13, a medium diameter flexible intravascular stent 150 for use in a body lumen includes a plurality of cylindrical rings 152 having a distal end cylindrical ring 154, a proximal end cylindrical ring 156, and a plurality of body cylindrical rings 158, all of the cylindrical rings being aligned along a common longitudinal axis and interconnected to form the stent. Each cylindrical ring having a first delivery diameter 160 and a second implanted diameter 162. At least some of the body cylindrical rings 152 have a plurality of first peaks 164 connected by first bar arms 166 and second peaks 168 connected by second bar arms 170. Each of the bar arms has a length, the second bar arms 170 of the second peaks 168 being shorter than the first bar arms 166 of the first peaks 164. At least one undulating link 172 attaches each cylindrical ring 152 to an adjacent cylindrical ring 152, the undulating links having a hinge 174 extending transverse to the stent longitudinal axis toward the second peak 168, the height of the second peak being sized so that as the stent is compressed to the first delivery diameter, the hinge 174 of the undulating link 172 is longitudinally aligned with and proximal to the second peak 168. The distal end cylindrical ring 154, the proximal end cylindrical ring 156, and the body cylindrical rings 158 have bar arms 176 having the same width 178. Each undulating link 172 has a long arm 180 and a short arm 182, the long arm 180 having multiple slight bends 184 along its length. A second to the proximal end cylindrical ring 186 has a first set of bar arms 188 having first widths 190 and a second set of bar arms 192 having second widths 194. The plurality of first peaks 164 and the plurality of second peaks 168 on the distal end cylindrical ring 154 have an inner radius 196 not to exceed 68 micron (0.0268 inch). The plurality of first peaks 164 and the plurality of second peaks 168 on the body cylindrical rings 158 have an inner radius 198 not to exceed 50 micron (0.00197 inch).

The stent of the present invention can be mounted on a balloon catheter which is well known in the prior art. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient, and the stent remains implanted in the artery. Similarly, if the stent of the present invention is made from a self-expanding metal alloy, such as nickel-titanium or the like, the stent may be compressed or crimped onto a catheter, and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter, or the catheter sheath is withdrawn proximally, and the stent is held in place until it exits the catheter and self-expands into contact with the wall of the artery. Balloon catheters and catheters for delivering self-expanding stents are well known in the art.

The stent of the present invention can be made in many ways. One method of making the stent is to cut a thin-walled tubular member, such as cobalt-chromium alloy tubing to remove portions of the tubing in the desired pattern for a stent, leaving relatively untouched the portions of the metallic tubing which are to form the stent. The stent also can be made from other metal alloys such as tantalum, nickel-titanium, stainless steel, titanium, shape memory and superelastic alloys, and the nobel metals such as gold or platinum. In accordance with the invention, it is preferred to cut the tubing in the desired pattern by means of a machine-controlled laser as is well known in the art.

The stent of the present invention also can be made from metal alloys other than stainless steel, such as shape memory alloys. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation or displaying stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein or a catheter without a balloon, or a sheath catheter.

While the invention has been illustrated and described herein, in terms of its use as an intravascular stent, it will be apparent to those skilled in the art that the stent can be used in other body lumens. Further, particular sizes and dimensions, number of undulations or U-shaped portions per ring, materials used, and the like have been described herein and are provided as examples only. Other modifications and improvements may be made without departing from the scope of the invention.

We claim:

1. A flexible intravascular stent for use in a body lumen, comprising:

a plurality of cylindrical rings comprising of a distal end cylindrical ring, a proximal end cylindrical ring, and a plurality of body cylindrical rings, all of the cylindrical rings being aligned along a common longitudinal axis and interconnected to form the stent, each cylindrical ring having a first delivery diameter and a second implanted diameter;

each cylindrical ring having a plurality of first peaks connected by bar arms and second peaks connected by bar arms, each of the bar arms having a length, the bar arms of the second peaks being shorter than the bar arms of the first peaks;

at least one undulating link attaching each cylindrical ring to an adjacent cylindrical ring, the undulating links having a curved portion extending transverse to the stent longitudinal axis toward the second peak, the height of the second peak being sized so that as the stent is compressed to the first delivery diameter, the curved portion of the undulating link is longitudinally aligned with and proximal to the second peak;

the distal end cylindrical ring having a first width for a first set of bar arms and a second width for a second set of bar arms; and each undulating link having a first arm and a second arm, the first arm having multiple slight bends along a length of the first arm, and the first arm being longer than the second arm, wherein the undulating link first arm and the undulating link second arm are substantially parallel to the stent longitudinal axis.

2. The stent of claim 1, wherein the body cylindrical rings having a third width for a third set of bar arms and a fourth width for a fourth set of bar arms.

3. The stent of claim 1, wherein the proximal end cylindrical ring having a fifth bar arm width for a fifth set of bar arms.

4. The stent of claim 1, wherein the plurality of first peaks and the plurality of second peaks on the distal end cylindrical ring have an inner radius not to exceed 68 micron (0.0268 inch).

5. The stent of claim 1, wherein the plurality of first peaks and the plurality of second peaks on the body cylindrical rings have an inner radius not to exceed 50 micron (0.00197 inch).

6. The stent of claim 1, wherein the first peaks of each cylindrical ring are in phase with the first peaks of an adjacent cylindrical ring.

7. The stent of claim 1, wherein the undulating links are configured to provide flexibility to the stent.

8. The stent of claim 1, wherein the stent is formed from a tube.

9. The stent of claim 1, wherein the stent is formed from a metal alloy.

10. The stent of claim 9, wherein the stent is formed from any of the group of metal alloys consisting of stainless steel, tantalum, nickel-titanium, cobalt-chromium and titanium.

11. The stent of claim 1, wherein the stent is coated with a therapeutic drug.

12. A flexible intravascular stent for use in a body lumen, comprising:
   a plurality of cylindrical rings comprised of a distal end cylindrical ring, a proximal end cylindrical ring, and a plurality of body cylindrical rings, all of the cylindrical rings being aligned along a common longitudinal axis and interconnected to form the stent, each cylindrical ring having a first delivery diameter and a second implanted diameter;
   each cylindrical ring having a plurality of first peaks connected by bar arms and second peaks connected by bar arms, each of the bar arms having a length, the bar arms of the second peaks being shorter than the bar arms of the first peaks;
   at least one undulating link attaching each cylindrical ring to an adjacent cylindrical ring, the undulating links having a curved portion extending transverse to the stent longitudinal axis toward the second peak, the height of the second peak being sized so that as the stent is compressed to the first delivery diameter, the curved portion of the undulating link longitudinally aligned with and proximal to the second peak;
   the distal end cylindrical ring and the plurality of body cylindrical rings have bar arms having the same width; and
   each undulating link having a first arm and a second arm, the first arm having multiple slight bends along a length of the first arm, the first arm being longer than the second arm, and wherein the undulating link first arm and the undulating link second arm are substantially parallel to the stent longitudinal axis.

13. The stent of claim 12, wherein the proximal end cylindrical ring has bar arm widths that are greater than the bar arm widths of the distal end cylindrical ring and the plurality of body cylindrical rings.

14. The stent of claim 12, wherein a second to the proximal end cylindrical ring has a first set of bar arms having first widths and a second set of bar arms having second widths.

15. The stent of claim 12, wherein the plurality of first peaks and the plurality of second peaks on the distal end cylindrical ring have an inner radius not to exceed 68 micron (0.0268 inch).

16. The stent of claim 12, wherein the plurality of first peaks and the plurality of second peaks on the body cylindrical rings have an inner radius not to exceed 50 micron (0.00197 inch).

17. A flexible intravascular stent for use in a body lumen, comprising:
   a plurality of cylindrical rings comprised of a distal end cylindrical ring, a proximal end cylindrical ring, and a plurality of body cylindrical rings, all of the cylindrical rings being aligned along a common longitudinal axis and interconnected to form the stent, each cylindrical ring having a first delivery diameter and a second implanted diameter;
   each cylindrical ring having a plurality of first peaks connected by bar arms and second peaks connected by bar arms, each of the bar arms having a length, the bar arms of the second peaks being shorter than the bar arms of the first peaks;
   at least one undulating link attaching each cylindrical ring to an adjacent cylindrical ring, the undulating links having a curved portion extending transverse to the stent longitudinal axis toward the second peak, the height of the second peak being sized so that as the stent is compressed to the first delivery diameter, the curved portion of the undulating link longitudinally aligned with and proximal to the second peak;
   the distal end cylindrical ring, the proximal end cylindrical ring, and the body cylindrical rings have bar arms having the same width; and
   each undulating link having a first arm and a second arm, the first arm having multiple slight bends along a length of the first arm, and the first arm being longer than the second arm, wherein the undulating link first arm and the undulating link second arm are substantially parallel to the stent longitudinal axis.

18. The stent of claim 17, wherein a second to the proximal end cylindrical ring has a first set of bar arms having first widths and a second set of bar arms having second widths.

19. The stent of claim 17, wherein the plurality of first peaks and the plurality of second peaks on the distal end cylindrical ring have an inner radius not to exceed 68 micron (0.0268 inch).

20. The stent of claim 17, wherein the plurality of first peaks and the plurality of second peaks on the body cylindrical rings have an inner radius not to exceed 50 micron (0.00197 inch).

* * * * *